United States Patent [19]

Walters

[11] 4,312,354
[45] Jan. 26, 1982

[54] PACEMAKER WITH CIRCUIT FOR PULSE WIDTH MODULATING STIMULUS PULSES IN ACCORDANCE WITH PROGRAMMED PARAMETER CONTROL STATES

[75] Inventor: Robert A. Walters, Murrysville, Pa.

[73] Assignee: ARCO Medical Products Company, Leechburg, Pa.

[21] Appl. No.: 118,060

[22] Filed: Feb. 4, 1980

[51] Int. Cl.³ .............................................. A61N 1/36
[52] U.S. Cl. ........................ 128/419 PG; 128/419 PT
[58] Field of Search .................... 128/419 PT, 419 PG

[56] References Cited

U.S. PATENT DOCUMENTS

| | | | |
|---|---|---|---|
| 3,833,005 | 9/1974 | Wingrove | 128/419 PG |
| 3,945,387 | 3/1976 | Adams | 128/419 PG |
| 4,126,139 | 11/1978 | Walters et al. | 128/419 PG |
| 4,187,854 | 2/1980 | Hepp et al. | 128/419 PG |
| 4,192,316 | 3/1980 | Walters et al. | 128/419 PG |

*Primary Examiner*—William E. Kamm
*Attorney, Agent, or Firm*—Bard, Groves, Sroufe, Ryerson & Jackson

[57] ABSTRACT

An implantable pacemaker having circuit means for indicating, by pulse width modulation of the delivered pacing pulses, the programmable control states which control the selected pacemaker operating perameters. The circuitry includes a parallel to serial shift register adapted to receive the control states from a pacer circuit and to generate a serial multiple bit word when the pacemaker is switched to a magnetic mode. The shift register is clocked by stimulus timing signals, and the multiple bit word drives a one shot generator, the output of which is combined with the timing pulses to produce pulse width modulated pacing pulses.

6 Claims, 3 Drawing Figures

PACEMAKER WITH CIRCUIT FOR PULSE WIDTH MODULATING STIMULUS PULSES IN ACCORDANCE WITH PROGRAMMED PARAMETER CONTROL STATES

CROSS REFERENCE TO RELATED APPLICATION

Reference is made to U.S. Pat. No. 4,190,055, issued Feb. 26, 1980, and assigned to the same assignee, titled "Circuit For Determining The Parameter Control States of An Implanted Pacer", which patent is incorporated by reference.

BACKGROUND OF THE INVENTION

This invention relates to improvements in heart pacemakers and, more particularly, to improvements in pacemakers of the type which are externally programmable so as to vary selected operating parameters and, more particularly, to the circuit means for generating signals in the implanted pacemaker to indicate the digital states controlling the operating parameters.

As set forth in the above referenced application, the prior art shows a variety of techniques adapted to pacemakers for externally controlling selected operating parameters after the pacemaker has been implanted in a patient. Parameters of interest may include the stimulation pulse amplitude, width and rate, as well as the refractory period the sensitivity to naturally occuring heart pulses, and the mode of operation.

U.S. Pat. No. 4,049,004, assigned to the assignee of the present invention, discloses a heart pacer having variable operating parameters which are controlled by digital circuitry responsive to externally applied magnetic pulses. Said U.S. Pat. No. 4,049,004 is incorporated herein by reference.

Referenced U.S. Pat. No. 4,190,555 provides a modification of the pacemaker of the referenced patent so as to provide pulse position modulation of the generated pacer pulses. In that arrangement, a delay is added between pulses when a particular logic state appears, and no delay is added if the compliment of that logic state appears. This means that the parameters can be determined externally by observing the successive periods between stimulation pulses when the pacer is placed in a magnetic mode.

SUMMARY OF THE INVENTION

It is an object of this invention to provide a pacemaker having circuit means for pulse width modulating asynchronously generated pacing signals in a way such as to indicate the programmed control states by which pacer operating parameters are controlled. The pacemaker of this invention may be a fully implantable pacer, which is programmed by external magnetic or electromagnetic means.

It is another object of this invention to provide, in a programmable and implantable pacemaker, a circuit modification which can be added without otherwise affecting the pacemaker operation, for modifying the pacing signals upon command in a way so as to indicate the control states which are controlling the operating parameters of the pacemaker.

It is another object of this invention to provide in an implantable programmable cardiac pacemaker a means for modulating delivered stimulus pulses in a manner so as to provide information concerning programmed operating parameters, while holding the pacing rate at a fixed asynchronous value.

In accordance with the above objects, there is provided a programmable heart pacer of the type having one or more operating parameters controllable in response to received externally generated program signals, the pacer having circuit means operable upon an external control for generating a serial parameter signal representing the control states of the operating parameters and modulating means for pulse width modulating the delivered stimulus pulses with the generated serial parameter signal, thereby providing observable indication of the programmed control states which represent the programmed operating parameters of the pacemaker.

DETAILED DESCRIPTION OF THE PREFERRED EMBODIMENTS

Figure 1:
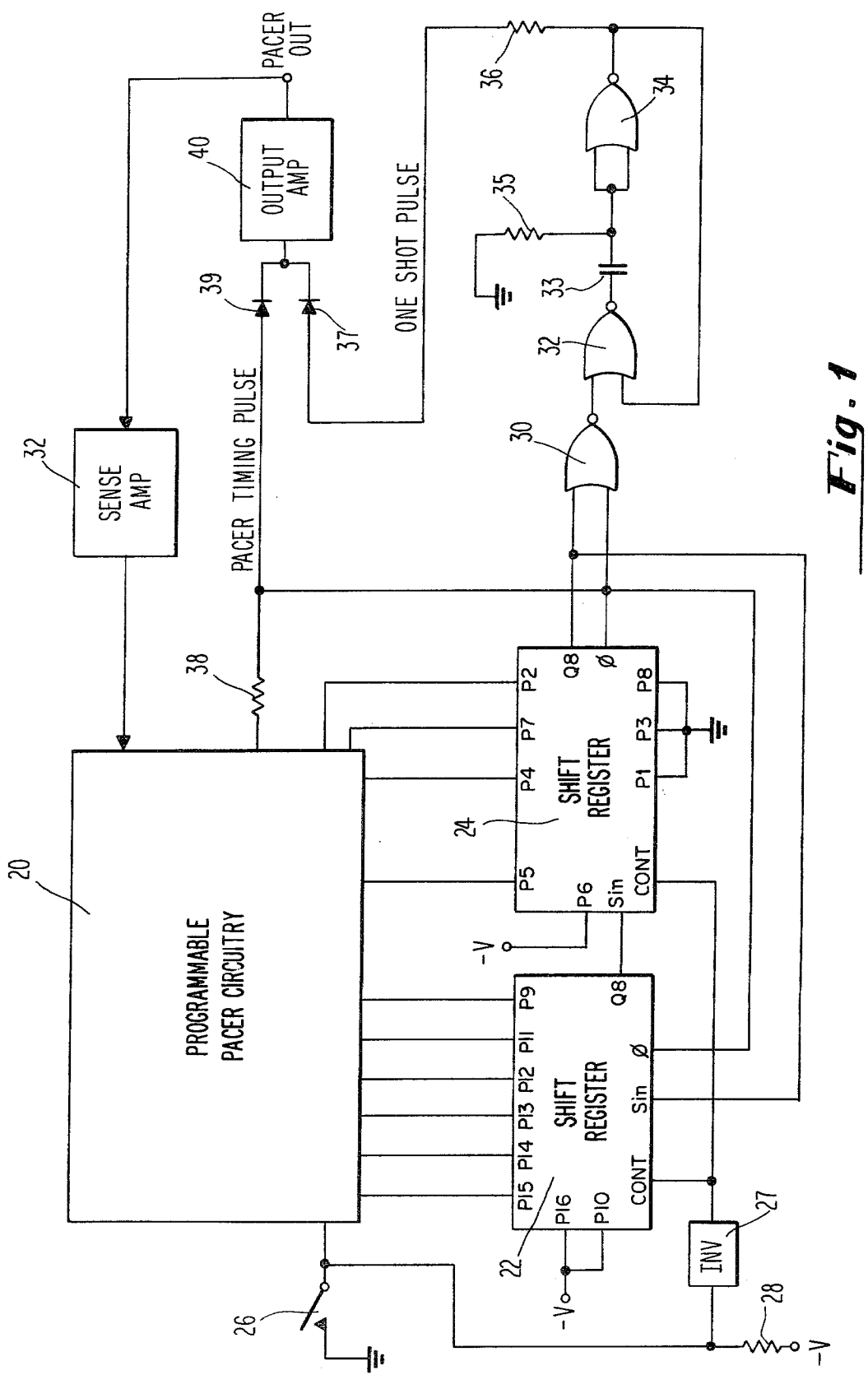
FIG. 1 is a block diagram showing the pacemaker of this invention, showing the pulse width modulation circuitry in detail and also illustrating the manner in which it is interconnected with remainder of the pacer circuitry.

Referring now to FIG. 1, programmable pacer circuitry 20 designated CHIP represents electronic circuitry of suitable design as used in a programmable pacemaker. This circuitry delivers pacer timing pulses through resistor 38, which are fed through to an output amplifier 40 for producing the delivered stimulus signals. The detected QRS signals, as utilized in a demand pacer, are sensed in sense amplifier 32 and inputted to programmable pacer circuitry 20. While the circuitry of programmable pacer circuitry 20 may be of a number of different designs, it is suitably as illustrated in FIG. 1 of the referenced patent. It is to be noted that the chip contains, as part of its parameter control circuitry, a register for storing a plurality of control states corresponding to the respective parameters to be controlled.

Still referring to FIG. 1, shift registers 22 and 24 are each 8 state registers, suitably type 4021 IC parallel to serial shift registers. IC 22 has six pins (P9 and P11–15) connected to respective stages of the parameter control register in programmable pacer circuitry 20, such that stages P9 and P11–15 are normally of the same logic state of the corresponding parameter control stages to which they are connected. Stages P10 and P16 are connected to $-V$, such that they are normally at logic 0. Correspondingly, shift register 24 has stages P2, P4, P5 and P7 connected to corresponding stages of the parameter control register in programmable pacer circuitry 20. Stages P1, P3 and P8 are tied to ground, such that they are normally at a logic high, while stage P6 is tied to $-V$ and is therefore normally at a low logic level. The output of register 22, at Q8, is connected to the signal in ($S_{in}$) terminal of register 24, while the output Q8 of register 24 is connected back to the $S_{in}$ terminal of register 22, thereby providing for recirculation when the logic states are shifted. The pacer timing pulses generated in programmable pacer circuitry 20 are connected to the clock terminal for both registers 22 and 24.

When an external programming signal is received, reed switch 26 or equivalent is closed. One side of switch 26 is connected to ground, and the other side is connected through resistor 28 to a supply maintained at −V. Thus, normally the input to inverter 27 is at a low state such that the output is at a high state. However, when switch 26 is closed, the high ground signal is connected to the input of the inverter, such that the output goes logic low. The output of inverter 27 is connected to the control input of each of the registers. Normally the high logic signal controls the registers to that each stage is held at a logic state corresponding to the logic state received from programmable pacer circuitry 20; when switch 26 is closed, the logic signals in the registers are circulated each time a pacer timing pulse is received, causing shifting of the states. The magnetic signal which closes 26 also causes the pacer to operate in a fixed rate or asynchronous mode, in a well known manner. Thus, when a magnetic signal is received from an external source, the data in the control register found in programmable pacer circuitry 20 is circulated to registers 22 and 24, providing a serial train of bits, or a word occuring at the output Q8 of register 24.

The pacer timing pulses in programmable pacer circuitry 20, and the logic state signals from Q8 of register 24 are inputted on separate input terminals of NOR gate 30, producing an output when a logic zero is present at the output of register 24. The gated signal triggers a monostable or one shot circuit of conventional design, comprised of NOR gate 32, capacitor 33, resistor 35 and inverter 34, connected as shown in FIG. 1. Since the triggering signal produced at the output of gate 30 is initiated at the trailing edge of the pacer timing pulse (when it goes from a logic high to a logic low), the one shot pulse is initiated substantially at the end of the pacer timing pulse. The one shot pulse is transmitted through resistor 36 and diode 37, and ORed into the input of output amplifier 40 along with pacer timing pulses which are connected through diode 39. Thus, when a one shot pulse is presented, the input to amplifier 40 lasts substantially the duration of the pacer timing pulse plus the time interval of the one shot pulse, such that the pacer output pulse is extended, i.e. pulse width modulated.

Figure 2:
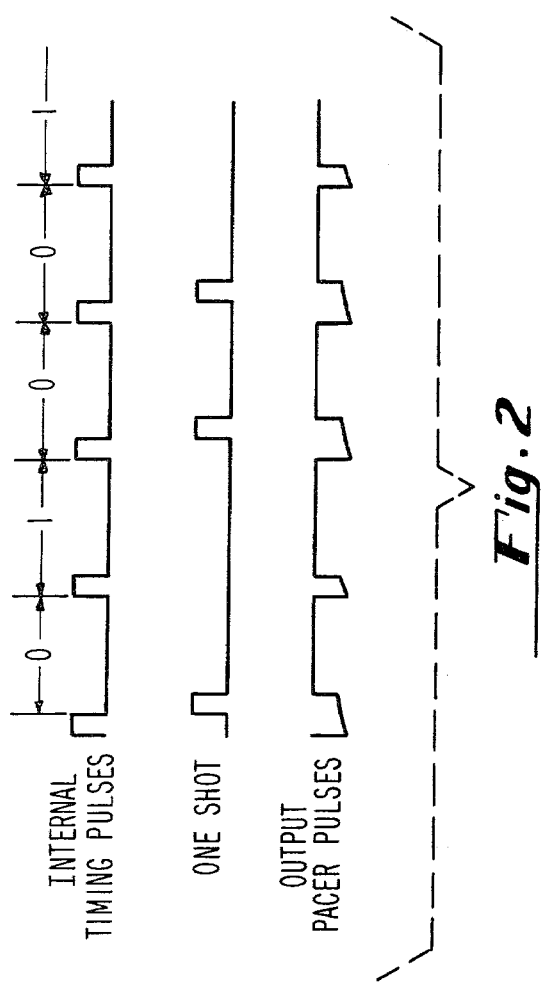
FIG. 2 is a series of three graphs showing timing signals utilized in producing the pulse width modulated pacer pulses.
Figure 3:
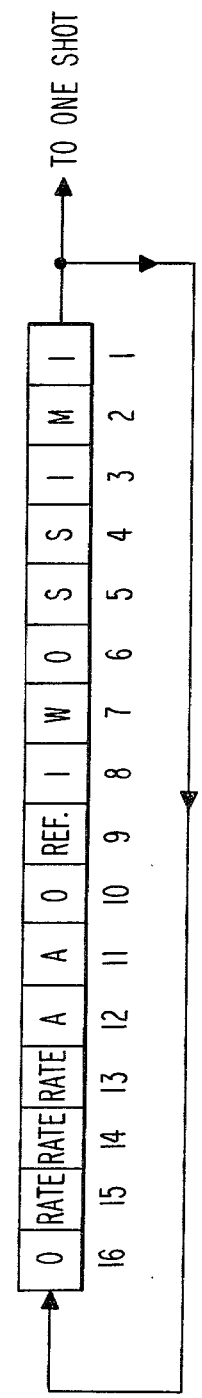
FIG. 3 is a schematic diagram illustrating the control states in the shift register utilized in the pacemaker of this invention, and the manner in which they are circulated during generation of the pulse width modulated pacing signals.

The timing, and manner of pulse width modulation is illustrated in FIG. 2. The very top line shows the logic level at the output of shift register 24. The next line shows the internal timing pulses, and note that the logic states are shifted at the beginning of each timing pulse. When a zero logic level is present at the output of register 24, the one shot pulse occurs substantially at the trailing edge of the internal timing pulse, such that the output pacer pulse (shown in the last curve) is extended in time duration. Corresponding to the presence of the logic one input at the gate 30, the output pacer pulse has a normal pulse width. Thus, the data being circulated through registers 22, 24 can be determined by examination of the pulse width modulation. Note that 6 of the 16 stages of the shift register are predetermined and therefore known, and this enables a determination of how the respective bits of the detected serial word correspond to the respective pacer parameters. FIG. 3 illustrates the data composition of the shift register when data is fixed, i.e. not being circulated. Stages, 1, 3, 6, 8, 10, and 16 have predetermined logic states, constituting a predetermined code which is known. Stage 2 corresponds to the mode of the pacer; stages 4 and 5 provide 2 bits which indicate that the sensitivity setting; stage 7 represents the pulse width setting; stage 9 represents the refractory interval setting; stage 11 and 12 represent the stimulus pulse amplitude setting; and stages 13, 14 and 15 represent the stimulus pulse rate setting.

There is thus disclosed a very simple and reliable technique for providing remote determination of the parameter settings of an implanted pacemaker. In operation, a conventional procedure is used to determine the EKG of a patient either by recording it on a strip chart, viewing it on a screen, or otherwise automatically detecting it. When the pacer is switched to an asynchronous or magnetic mode by application of an external signal, the resulting asynchronous stimulus pulses are pulse width modulated, successive pulses being modulated in correspondence with respective bits representing stored logic states in the pacer parameter control, thereby providing information for determination of programmed pacer variables such as pacer mode, sensitivity, stimulus width, refractory period, stimulus amplitude, stimulus rate and the like.

What is claimed is:

1. A programmable heart pacer for generating stimulus pulses, said pacer having controllable operating parameters, and having a control circuit responsive to an externally generated program signal which is received by said pacer, said control circuit controlling one or more selected operating pacer parameters, each of said parameters having a corresponding control state, comprising:

generating means for generating one or more parameter signals in a known sequence, said parameter signals corresponding to the control states of selected operating parameters; and modulating means for pulse width modulating said pacer stimulus pulses with, said selected operating parameter signals, to provide a signal indicative of said control states and thus of one or more operating parameters.

2. The heart pacer of claim 1, wherein said generating means comprises means for generating a plural bit serial binary word representative of said control states, and wherein said modulating means pulse width modulates a series of stimulus pulses to encode thereon pulse width information relating to the control states of said operating parameters.

3. The heart pacer of claim 2, wherein said generating means comprises a shift register and said modulating means comprises a one shot circuit connected to the output of said shift register.

4. The heart pacer of claim 3, wherein said heart pacer has means for generating stimulus timing pulses, and said modulating means comprises means for combining said one shot pulses and said timing pulses to provide width modulated timing pulses.

5. The heart pacer of claim 1, wherein said control circuit has a register containing a plurality of logic states established by a received program signal, and controlling circuitry for controlling said operating parameters with said logic states, and wherein said generating means comprises means for generating a serial pulse signal representative of the bit data of said register logic states, and said modulating means comprises means for pulse width encoding successive stimulus pulses in accordance with the successive data bits of said serial pulse signal.

6. A programmable heart pacer for generating stimulus pulses, said pacer having controllable operating parameters, and having a control circuit responsive to an externally generated program signal which is received by said pacer, said control circuit controlling one or more selected operating pacer parameters, each of said parameters having a corresponding control state, comprising:
- a shift register for normally storing data bits representing parameter control states;
- means for shifting the data in said shift register with stimulus timing pulses to produce a series of data signals;
- means for generating time delayed signals from said series of said signals;
- means for adding said stimulus timing pulses and said time delay pulses to get pulse width modulated timing pulses; and
- means for generating pacing pulses indicative of parameter control states in response to said pulse width modulating timing pulses.

* * * * *

UNITED STATES PATENT AND TRADEMARK OFFICE
CERTIFICATE OF CORRECTION

PATENT NO. : 4,312,354
DATED : January 26, 1982
INVENTOR(S) : Robert A. Walters

It is certified that error appears in the above—identified patent and that said Letters Patent is hereby corrected as shown below: ON THE TITLE PAGE, In The Abstract at line 4, delete "perameters" and insert --parameters--.

In the specification, at column 1, line 8, delete "APPLICATION" and insert --PATENT--; at line 30, after "period", insert --,--; at line 38, delete "4,190,555" and insert --4,190,055--; at line 52, delete "asychronously" and insert --asynchronously--.

At column 2, line 21, after "with", insert --the--.

At column 3, line 13, delete "to" and insert --so--.

At Claim 1, line 14, after "with", delete ",".

At Claim 4, line 5, after "provide", insert --pulse--.

At Claim 6, line 21, delete "modulating" and insert --modulated--.

Signed and Sealed this

Twenty-fifth Day of May 1982

[SEAL]

Attest:

Attesting Officer

GERALD J. MOSSINGHOFF
Commissioner of Patents and Trademarks